United States Patent
Kolb

(10) Patent No.: US 9,372,180 B2
(45) Date of Patent: Jun. 21, 2016

(54) INSPECTION AND RECYCLING OF CONTAINERS

(75) Inventor: Herbert Kolb, Teugn (DE)

(73) Assignee: KRONES AG, Neutraubling (DE)

( * ) Notice: Subject to any disclaimer, the term of this patent is extended or adjusted under 35 U.S.C. 154(b) by 99 days.

(21) Appl. No.: 14/354,525

(22) PCT Filed: Aug. 3, 2012

(86) PCT No.: PCT/EP2012/065274
§ 371 (c)(1),
(2), (4) Date: Jun. 6, 2014

(87) PCT Pub. No.: WO2013/068136
PCT Pub. Date: May 16, 2013

(65) Prior Publication Data
US 2014/0294238 A1    Oct. 2, 2014

(30) Foreign Application Priority Data

Nov. 10, 2011 (DE) .......................... 10 2011 086 099

(51) Int. Cl.
| | |
|---|---|
| *G06K 9/00* | (2006.01) |
| *G01N 33/14* | (2006.01) |
| *G01N 21/90* | (2006.01) |
| *G06T 7/00* | (2006.01) |

(52) U.S. Cl.
CPC ............ *G01N 33/14* (2013.01); *G01N 21/9027* (2013.01); *G06T 7/0008* (2013.01); *G06T 2207/10048* (2013.01); *G06T 2207/30128* (2013.01); *G06T 2207/30242* (2013.01)

(58) Field of Classification Search
CPC .................... G06Q 10/30; G06T 2207/30242; G06T 7/0008
See application file for complete search history.

(56) References Cited

U.S. PATENT DOCUMENTS 4,136,930 A * 1/1979 Gomm ............... G01N 21/8851
250/223 B (Continued)

FOREIGN PATENT DOCUMENTS

| AU | WO 0179829 A1 * 10/2001 ........... G01N 29/036 |
| CN | 101210885 A     7/2008 |

(Continued)

OTHER PUBLICATIONS

Kamath, Sapna, et al. "The influence of temperature on the foaming of milk." International dairy journal 18.10 (2008): 994-1002.*

(Continued)

*Primary Examiner* — Stephen R Koziol
*Assistant Examiner* — Jonathan S Lee
(74) *Attorney, Agent, or Firm* — Marshall, Gerstein & Borun LLP

(57) ABSTRACT

A method for examining filled containers, which are filled with $CO_2$-containing products such as beer or lemonade, for contaminants such as glass fragments, including examining, e.g. by means of a camera, a container for gas bubbles in the product/in the container and/or for gas mists in the container, and sorting out the container, if gas bubbles are determined in the product and/or if $CO_2$ mists are determined in the container, and re-examining the container at a later time.

15 Claims, 1 Drawing Sheet

(56) References Cited

U.S. PATENT DOCUMENTS

| | | | | |
|---|---|---|---|---|
| 5,067,616 A | * | 11/1991 | Plester | B07C 5/3408 209/3.1 |
| 5,536,935 A | * | 7/1996 | Klotzsch | G01N 21/51 209/582 |
| 5,864,395 A | * | 1/1999 | Laurberg | G01N 21/9027 250/223 B |
| 6,275,603 B1 | * | 8/2001 | Cronshaw | G01N 21/9027 250/223 B |
| 7,693,322 B2 | * | 4/2010 | Carroll | G01N 13/02 382/100 |
| 2002/0155211 A1 | * | 10/2002 | Yokoo | A23L 2/02 426/599 |
| 2008/0001104 A1 | * | 1/2008 | Voigt | G01N 21/9027 250/559.46 |
| 2008/0002182 A1 | * | 1/2008 | Akkerman | G01N 21/9045 356/73 |
| 2008/0161947 A1 | | 7/2008 | Niedermeier | |
| 2010/0225908 A1 | * | 9/2010 | Kwirandt | B07C 5/3408 356/239.4 |
| 2011/0025840 A1 | * | 2/2011 | Fiegler | G01N 21/9027 348/127 |
| 2011/0233410 A1 | * | 9/2011 | Niedermeier | G01N 21/9027 250/358.1 |
| 2013/0113939 A1 | * | 5/2013 | Strandemar | G06T 5/10 348/164 |
| 2015/0339510 A1 | * | 11/2015 | Bolea | G06K 9/00134 382/133 |
| 2016/0069801 A1 | * | 3/2016 | Stevens | G01N 21/4788 348/135 |

FOREIGN PATENT DOCUMENTS

| | | |
|---|---|---|
| CN | 101354359 A | 1/2009 |
| CN | 102200520 A | 9/2011 |
| DE | 10257749 B4 | 5/2006 |
| EP | 1939630 A2 | 7/2008 |
| EP | 2369328 A2 | 9/2011 |
| EP | 2383567 A1 | 11/2011 |
| JP | H09325122 A | 12/1997 |
| WO | WO-9714956 A1 | 4/1997 |

OTHER PUBLICATIONS

PCT Search Report for International Application No. PCT/EP2012/065274, dated Oct. 22, 2012.

PCT Notification of Transmittal of Translation of the International Preliminary Report on Patentability and Written Opinion of the International Searching Authority, May 22, 2014.

Chinese Office Action Application No. 201280055437.4, dated Jun. 16, 2015.

* cited by examiner

INSPECTION AND RECYCLING OF CONTAINERS

CROSS-REFERENCE TO RELATED APPLICATION

This application is the U.S. national phase of International Patent Application No. PCT/EP2012/065274, filed Aug. 3, 2012, which claims priority to German Application No. 10 2011 086 099.1 filed Nov. 10, 2011. Applications PCT/EP2012/065274 and DE 10 2011 086 099.1 are hereby incorporated by reference.

FIELD OF THE DISCLOSURE

This disclosure relates to a system and a method for inspecting filled containers, e.g. bottles, whose content may e.g. be charged with $CO_2$.

BACKGROUND

DE 102 57 749 B4 discloses an inspection machine that inspects containers, which are filled with a product and closed, for contaminants, e.g. glass fragments. To this end, the container is first caused to rotate about its own axis until the product, the liquid, (partially) follows the rotation. Subsequently, the container is stopped while the liquid continues to rotate. In this condition, the container is illuminated and observed by means of a camera. In this so-called spin-stop process, the motion of the liquid cannot be seen in the camera image, whereas the contaminant and its motion are visible.

Contaminants may be the following ones: glass fragments or other solid matter that are not desired in the product, in particular glass fragments are dangerous to the consumer.

WO9714956A1 discloses that, depending on the $CO_2$ content and the degree of dissolution of the $CO_2$ in the product, fine gas bubbles may form in $CO_2$-containing products, such as beer, cola, lemonade and others, during rotation about the bottle's own axis. These gas bubbles as well as possible foreign bodies move in the product and in a bottle, respectively. Differentiating gas bubbles and foreign bodies according to the above-mentioned spin-stop method is hardly possible in such cases.

The possibility that bottles may be discharged/sorted out by mistake due to gas bubbles instead of foreign bodies is given. This could be minimized through a long dwell time between filling and inspection, but this necessitates long transport distances or very large bulk conveyors. Such technical retrofitting is, moreover, complicated and leads to an increase in production costs.

The formation of undesired gas bubbles in $CO_2$-containing products may be caused not only by the inspection process itself but also by various other disturbances in a $CO_2$-containing product in the course of its production cycle.

Task

It is therefore the object of the present disclosure to provide an apparatus and a method, which improve/minimize the error rate during inspection/examination of containers that are filled with $CO_2$-containing products, such as beer, cola or lemonade.

SUMMARY OF THE DISCLOSURE

For the sake of completeness, it should here be mentioned that, when containers are referred to in the following, filled containers are meant, in particular containers filled with $CO_2$-containing products.

During the examination of filled containers, which are filled with $CO_2$-containing products such as beer or lemonade, for contaminants such as glass fragments, the containers can be examined for gas bubbles in the product/in the container and/or for a gas mist in the product/in the container. If this examination results in a determination of gas bubbles in the product/container and/or of gas mists in the product/container, these containers can first be sorted out, so as to be examined at least once more, before they either pass the renewed examination for contaminants without being objected to or before they are sorted out and removed from the production process once and for all.

This has the advantage that containers, which, although they contain gas bubbles in the product or a gas mist, are not contaminated, can be re-examined later on. During the period between two examinations, possibly existing gas bubbles or gas mists in the container may disappear in that they dissolve again in the product. Containers, which are not contaminated, but which only contained gas bubbles in the product and/or a gas mist during a first examination, and which are found to be deficiency-free/contaminant-free during renewed examination, can be recycled into the production process. The error rate of containers, which are not contaminated and which are discharged and removed from the production process by mistake, can thus be reduced in comparison with processes in which, e.g. in response to a detection of gas bubbles in the product, the containers in question are removed from the production process without renewed examination.

Containers in which contaminants, such as glass fragments, have been determined during the first examination, can, of course, be discharged/sorted out after the first examination and removed from the further production process once and for all, whereas containers in which neither contaminants nor gas bubbles in the product nor gas mists have been detected, can pass the examination without being objected to and advanced to further steps in the production process.

The examination of containers, which are filled with $CO_2$-containing products, for contaminants, such as glass fragments, can be executed by means of optical/infrared/photometric and/or light-microscopic methods, such as bright-field and/or dark-field microscopy, phase-contrast, interference-contrast, fluorescence, polarization and confocal microscopy, within the framework of a spin-stop process of the type mentioned at the beginning and described in WO97/14956A1. During spin-stop processes, the container is caused to rotate, so that the content of the container starts to rotate. Subsequently, when the container has been stopped, two, three or more successive pictures are taken, in the case of which the container content moved between two respective pictures, whereas the container did not move (with respect to the camera). By comparing the two pictures, conclusions can be drawn with respect to moving contaminants and/or gas bubbles. The spin-stop process can be executed while the containers are positioned on a carousel comprising a plurality of accommodation sites for containers, at which a respective one of the containers can be caused to rotate.

The differentiation between contaminants, gas bubbles in the product/in the container can be based e.g. on an analysis of a color/gray level spectrum with respect to contrast and/or brightness and/or color/gray level values in a camera image. It is e.g. possible to define threshold values in the differences and/or ratios of brightness and/or contrast between an object, for example a contaminant (e.g. a piece of broken glass), a gas bubble and the product, i.e. the content provided in the container.

The identification/classification of various objects in the container can be defined e.g. through a brightness threshold value that is exceeded or underrun e.g. by at least 1, 10, 100% with respect to the difference of the brightness of objects, e.g. objects/areas in the order of magnitude of at least 0.01, 0.1, 1, 10, 20 mm (or more), in comparison with the product/container content provided.

The position of detected objects within the container as well as their number and/or spatial dimensions may also/additionally be used for determining/identifying the objects in the container. For example, a minimum number of 10, 100 or 1000 objects with spatial dimensions, e.g. in an order of magnitude of at least 0.01, 0.1, 1, 10, 20 mm, and/or dwell positions of objects in the container within predetermined image areas may be used for classifying objects as gas bubbles and/or contaminants.

In the case of a large number of gas bubbles, it may perhaps no longer be possible to identify them individually, since they appear collectively as a mist. The presence of such a gas mist may e.g. be defined in that on a camera image, or on an image derived from one or a plurality of camera images, e.g. at the center of the container, large areas (having spatial dimensions of at least 0.1, 0.5, 1.0, 2.0 cm) underrun or exceed a color and/or gray value and/or brightness and/or contrast threshold value with respect to the provided product/container content by e.g. at least 1, 10, 100%, and/or in that said large areas exhibit a variation/variations of less than a maximum of 40, 30, 10% with respect to the mean value or median of the distribution of color and/or gray values and/or brightness and/or contrast values within said large areas, and/or the large areas with values for color and/or gray values and/or brightness and/or contrast values deviating from the container product in above-described way follow the inner contour of the container as regards their shape.

The detection of a gas mist in the product can be executed on the basis of a single recorded image, without a difference between two images from the spin-stop process being necessary. For detecting individual contaminants or gas bubbles, a differential image originating e.g. from a spin-stop process should preferably be evaluated.

Instead of using threshold values, which concern the contrast and/or brightness and/or color/gray level value in a camera image or in an image derived from one or a plurality of camera images, for classifying various objects or various areas in a filled container, also ranges of values for contrast and/or brightness and/or color/gray level values may be used.

It is also imaginable to classify/identify various objects, or various areas in a filled container, through infrared images, on the basis of different temperatures of the objects/large areas in the filled container. Also in this case, threshold values and ranges of values can be defined, e.g. threshold values for differences in temperature of at least 0.1, 0.5, 10, 20° C.

Likewise or additionally, objects in the container can be classified on the basis of their shape. Objects in the container may, by way of example, be identified as gas bubbles, if the numerical eccentricity of their projected contour in the camera image, or in an image derived from one or a plurality of camera images, is not larger than e.g. 0.1, 0.2, 0.3.

After an examination of containers, which are filled with $CO_2$-containing products, such as beer, cola or lemonade, and in which gas bubbles were detected in the product/container and/or contaminants were detected in the container, these containers can be marked, e.g. by an imprint or a label. A possible continuous circulation of rejected containers in the production process can thus be avoided. If contaminants are detected, the containers can be discharged once and for all (even if they have been neither marked nor labeled).

DETAILED DESCRIPTION OF THE PREFERRED EMBODIMENTS

Figure 1:
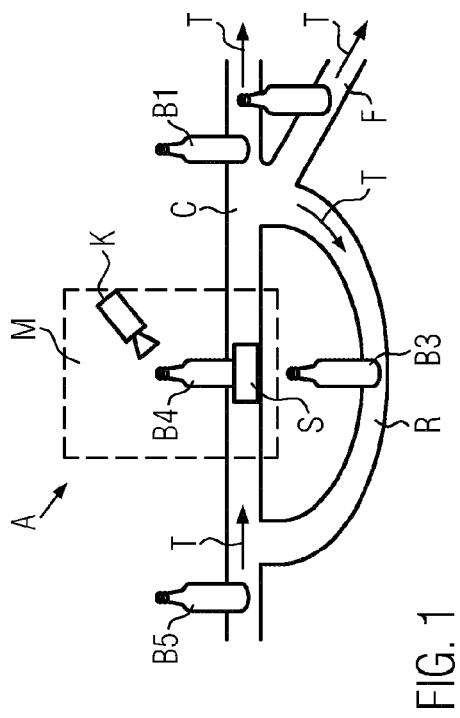
FIG. 1: is an isometric view of a system for examining filled containers.

FIG. 1 shows exemplarily a system A for inspecting whether filled containers, which are filled with $CO_2$-containing products such as beer or lemonade, contain contaminants such as glass fragments. A measurement unit M may here examine a container with a camera K, the container undergoing e.g. a spin-stop process through the container treatment unit S. Depending on the result of the examination, the measurement unit can advance an examined container to one of the three container guides, e.g. to container conveyor belts R, M or C. Instead of container conveyor belts also other transport facilities may be provided, e.g. facilities provided with movable grippers for gripping the containers.

A non-rejected container, in which neither contaminants nor gas bubbles in the product nor gas mists in the container were detected, may leave the measurement unit M, e.g. on conveyor belt C, and may be advanced to the next production step.

Containers in which contaminants, such as pieces of broken glass, were detected and/or containers in which gas bubbles in the product or gas mists in the containers were detected again, can be discharged/removed from the production process via the conveyor belt F.

The examination of the containers can lead e.g. to three different detection results, e.g. "free from contaminants", "contaminated" and "contains bubbles and/or mists". Depending on the detection result, the respective containers are advanced in different ways.

Containers in which gas bubbles in the product and/or gas mists in the container were detected during a first examination can be recycled via a conveyor belt R for renewed examination through the measurement unit M. It is, however, also imaginable that the conveyor belt R may lead such containers to some other measurement unit that is different from said measurement unit M.

Likewise, the system A for examining filled containers may include a parking station in which filled containers, which were sorted out for renewed examination for contaminants, can, prior to said renewed examination for contaminants, be parked e.g. for periods of at least 0.1, 1, 10, 100 h. The supply to the parking station may take place e.g. via the conveyor belt R or a further additional conveyor belt RZ (or other container transport facilities). This is advantageous insofar as the period between two examinations of the same filled container for contaminants can be controlled, irrespectively of and/or in addition to the conveying speed of the conveyor belts/of a conveyor belt.

Figure 2:
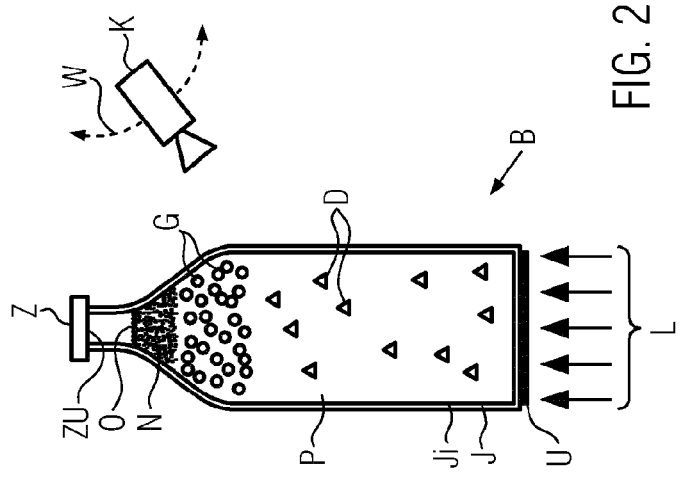
FIG. 2: is a plan view of an inspection of a filled container.

FIG. 2 shows exemplarily a container B filled with a product P and closed with a closure Z. A gas mist N is shown, which is composed of many gas bubbles that can no longer be resolved individually by a camera image. In addition, gas bubbles G as well as contaminants D are exemplarily identified.

Through the container bottom, light L falls exemplarily into the container B, so that the content of the container can be examined. The light L may also impinge on the container from the side or from above. A camera K, which is exemplarily arranged on the side and which is additionally able to move e.g. along the direction of movement W, is capable of taking pictures of the container and/or its content.

The inner side Ji of the container wall J, which is connected to the lower side ZU of the closure, defines the inner contour of the container.

Figure 3:
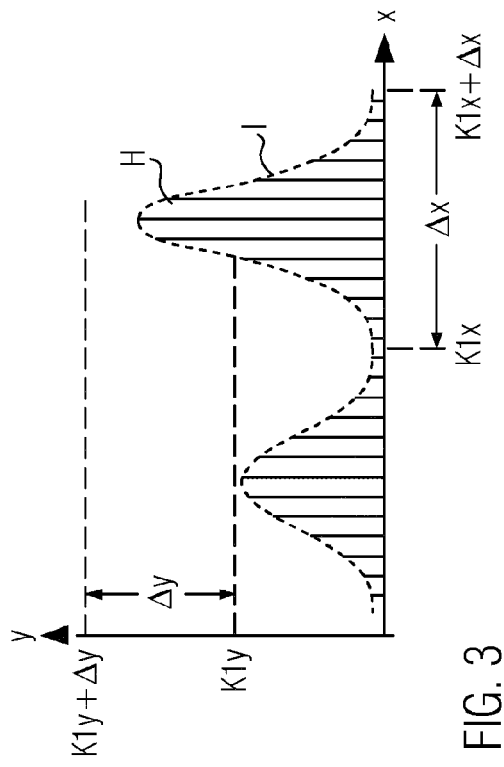
FIG. 3: is a plot of frequencies of various grey levels, within a filled container, by which images may be evaluated.

FIG. 3 shows a diagram, which illustrates exemplarily various evaluation possibilities of pictures of a container to be examined for contaminants, said pictures being e.g. pictures taken by a camera/derived pictures. For example, the X-axis may represent various gray levels in an examination image and the Y-axis may represent the frequencies of the gray levels. The frequency distribution of the gray levels, for example, may here be represented/used as a histogram H, or e.g. an interpolation I of the histogram H. By defining threshold values such as K1x and/or K1y or ranges of values K1x+Δx and/or K1y+Δy, it is thus possible to define gray level threshold values and/or ranges of gray level values so as to identify/classify various objects in the container, e.g. gas mists. Analogously, the X-axis may represent color grades, contrast/brightness levels, wavelength, frequency etc., and the Y-axis may represent e.g. intensity, power spectral density, etc. Likewise, the threshold values K1xK1y and the ranges of values K1x+Δx and/or K1y+Δy may represent the above-mentioned magnitudes.

Followed by X sheets with X figures, in which the following reference numerals are used:

A apparatus/system for inspecting/examining containers filled with $CO_2$-containing products.

B, B1, B2, B3, B4, B5 filled containers/receptacles.

C container conveyor belt/conveyor belt for advancing non-rejected containers.

F container conveyor belt/conveyor belt for discharging rejected containers from the production process.

R container conveyor belt/conveyor belt/recycling belt for recycling containers for renewed examination for contaminants.

S container treatment unit for spin-stop process.

T container conveying direction.

K camera, e.g. infrared camera, video camera, photo camera, etc.

N gas mist.

G gas bubbles.

D contaminants, e.g. pieces of broken glass, glass fragments.

P product/content provided in the container.

Z closure of the container.

ZU lower side of the closure of the container.

O surface of the product/content provided in the container.

L light.

U container bottom.

J container wall

Ji inner side of the container wall.

W degree of freedom/direction of movement for the camera.

H histogram.

I interpolation curve of the histogram H.

X ordinate of an image evaluation diagram, e.g. gray levels, color grades, contrast/brightness levels, wavelength, frequency, etc.

Y abscissa of an image evaluation diagram, e.g. frequency, intensity, power spectral density, etc.

K1x threshold value for ordinate magnitude.

K1y threshold value for abscissa magnitude.

Δx, Δy desired range of values for analysis of an ordinate/abscissa magnitude.

What is claimed is:

1. A method for examining filled containers which are filled with CO2-containing products for contaminants, comprising examining a container for at least one of gas bubbles in a product with which the container is filled or in the container, or gas mists in the product or container; and sorting out the container if at least one of gas bubbles are identified in the product or container, or if gas mists are identified in the product or container; and re-examining the sorted out container at a later time,
wherein gas mists are identified in the product or container by determining, within at least one large area with spatial dimensions of at least 0.1 cm, that at least one variation of less than a maximum of 40% with respect to at least one of the mean value or the median of the distribution of at least one of color, grey values, brightness, or contrast values within the at least one large area is exhibited.

2. The method according to claim 1, wherein examining the filled containers includes a spin-stop process.

3. The method according to claim 1, further comprising that gas bubbles in the product or container are determined if at least one of: a minimum number of objects is detected in at least one of the product or the container; objects are detected in at least one of the product or container having spatial dimensions of at least 0.01 mm; or said objects are detected at predetermined dwell positions.

4. The method according to claim 1, comprising that the at least one large area is on an image derived from at least one camera image of the container.

5. The method according to claim 1, comprising that objects in the container are classified on the basis of their shape, objects in the container being classifiable as gas bubbles if the numerical eccentricity of their projected contour in the camera image, or in an image derived from at least one camera image, is not larger than at least 0.1.

6. The method according to claim 1, comprising that at least one of gas bubbles in the product, gas mists in the container, or contaminants in the container is determined in that threshold values for temperature differences of at least 0.1° C. are used for differentiating between at least one of classifying the various objects or areas in the container.

7. The method according to claim 1, comprising that containers which are filled with CO2-containing products and in which contaminants have been determined during a first examination are at least one of marked, by means of an imprint or a label, or discharged from the production process, and containers which are filled with CO2-containing products and in which neither contaminants nor gas bubbles have been determined in the product or container nor gas mists have determined in the product or container are advanced to a next production step without being objected to.

8. The method according to claim 1, comprising that containers which are filled with CO2-containing products are discharged from the production process if at least one of contaminants, gas bubbles in the product or container, or gas mists in the product or container are determined during a re-examination of the container.

9. The method according to claim 1, comprising that filled containers, which have been sorted so that they can be examined for contaminants once more, are parked, prior to said renewed examination for contaminants, for periods of at least 0.1 h.

10. An apparatus for examining filled containers, which are filled with CO2-containing products, for contaminants, comprising a measurement unit comprising a camera which obtains at least one image of a container to be examined for at least one of gas bubbles in the product or container, gas mists in the product or container, or for contaminants in the product or container, in which, if gas bubbles are determined in at least one of the product or the container, or if gas mists are determined in the product or container, the container is sorted out and fed back to the measurement unit by a container guide for renewed examination later on, wherein gas mists are determined in the product or container when, within at least one large area with spatial dimensions of at least 0.1 cm, at least one variation of less than a maximum of 40% with respect to at least one of the mean value or the median of the distribution of at least one of color, grey values, brightness, or contrast values within the at least one large area is exhibited.

11. The apparatus according to claim 10, the apparatus for examining filled containers including a spin-stop container treatment unit for a spin-stop process.

12. The apparatus according to claim 10, the measurement unit including an infrared camera.

13. The method according to claim 4, wherein gas mists are identified in the product or container by determining that the image underruns or exceeds at least one of a color value, a gray value, a brightness, or a contrast threshold value with respect to the at least one of the product or container content by at least 1%.

14. The method according to claim 1, wherein gas mists in the product or container are determined to be present when the at least one variation follows an inner contour of the container as regards their shape.

15. A method for examining containers, which are filled with $CO_2$-containing product, for contaminants, the method comprising:
    examining at least one of the containers with a camera for gas mist in at least one of the product and the container;
    sorting out the container if gas mist is determined to be in the product or container; and
    re-examining the sorted out container at a later time,
    wherein gas mist is determined to be in the product or container when, in at least one large area with spatial dimensions of at least 0.1 cm on an image of the container obtained with the camera, at least one variation of less than 40% of at least one of the mean value or the median of the distribution of at least one of color, grey values, brightness, or contrast values within the at least one large area is exhibited.

* * * * *